United States Patent
Weuthen et al.

Patent Number: 5,631,357
Date of Patent: May 20, 1997

[54] NONIONIC EMULSIFIERS

[75] Inventors: Manfred Weuthen, Solingen; Petra Riegels, Leichlingen; Irmgard Hartel, Duesseldorf, all of Germany

[73] Assignee: Henkel Kommanditgesellschaft auf Aktien, Duesseldorf, Germany

[21] Appl. No.: 553,313

[22] PCT Filed: May 13, 1994

[86] PCT No.: PCT/EP94/01552

§ 371 Date: Jan. 26, 1996

§ 102(e) Date: Jan. 26, 1996

[87] PCT Pub. No.: WO94/28006

PCT Pub. Date: Dec. 8, 1994

[30] Foreign Application Priority Data

May 21, 1993 [DE] Germany .......................... 43 17 089.7

[51] Int. Cl.$^6$ .............................. C07G 3/00; C07H 15/04; C07H 1/06
[52] U.S. Cl. ..................... 536/18.6; 536/18.5; 536/127; 536/4.1
[58] Field of Search .................... 536/18.6, 18.5, 536/127, 4.1

[56] References Cited

FOREIGN PATENT DOCUMENTS

| | | |
|---|---|---|
| 0165721 | 12/1985 | European Pat. Off. . |
| 0492397 | 7/1992 | European Pat. Off. . |
| 4033928 | 4/1992 | Germany . |
| WO9206778 | 4/1992 | WIPO . |
| WO9310133 | 5/1993 | WIPO . |

*Primary Examiner*—John Kight
*Assistant Examiner*—Everett White
*Attorney, Agent, or Firm*—Ernest G. Szoke; Wayne C. Jaeschke; Real J. Grandmaison

[57] ABSTRACT

A process for making nonionic emulsifiers involving the steps of: (a) performing an acid-catalyzed acetalization reaction on a mixture of (i) sugars or water-containing starch degradation products and (ii) primary alcohols in a molar ratio of (i):(ii) of from 1:2 to 1:8; (b) terminating the reaction at a conversion ranging from 60% to 90% of the theoretical to form a reaction product; (c) neutralizing the reaction product to form a neutralized reaction product; and (d) purifying the neutralized reaction product by back-mixing the product through at least one coarse filter until the product becomes clear.

10 Claims, No Drawings

NONIONIC EMULSIFIERS

BACKGROUND OF THE INVENTION

1. Field of the Invention

This invention relates to nonionic emulsifiers obtained by acid-catalyzed acetalization of sugars with excess fatty alcohols, the conversion being limited to 60 to 90% of the theoretical, neutralization and filtration with back-mixing, to a process for their production and to their use for the production of surface-active preparations.

2. Discussion of Related Art

Alkyl oligoglycosides and, more particularly, alkyl oligoglucosides are nonionic surfactants which are acquiring increasing significance by virtue of their excellent detergent properties and their high ecotoxicological compatibility. They are produced from sugars or starch degradation products which are normally acetalized in the presence of acidic catalysts. For reasons associated with the law of mass action, it is advisable continuously to remove the water of condensation from the reaction equilibrium and to use one component, usually the less expensive fatty alcohol, in an adequate excess. On completion of the reaction, the acidic catalyst is neutralized, for example with sodium hydroxide and/or magnesium oxide, and the excess fatty alcohol is distilled off, usually to a residual content of <1% by weight. To obtain light-colored products, it has proved to be necessary in this regard to limit the percentage content of unreacted sugar to 1% by weight and preferably to 0.5% by weight or, in other words, to aim at a substantially quantitative conversion.

In addition to alkyl oligoglycosides, surfactant compounds containing the corresponding fatty alcohol as second component have proved to be particularly skin-compatible emulsifiers in the field of cosmetics. The preparation of such mixtures is comparatively simple and, in general, merely involves simply leaving the fatty alcohol present in excess during the production of the alkyl oligoglycosides in the product.

Thus, the use of a mixture containing 60 to 90% by weight of a $C_{12-22}$ fatty alcohol, 10 to 90% by weight of an alkyl oligoglycoside of corresponding chain length and optionally 0.5 to 5% by weight of a glycoside for the production of emulsions is known, for example, from WO 92/06778 (Seppic).

In addition, o/w emulsions containing 5 to 30% by weight of a water-insoluble oil, 2 to 15% by weight of a $C_{18-22}$ alkyl oligoglucoside, 2 to 20% by weight of a fatty acid partial glyceride and optionally linear saturated fatty alcohols are claimed in DE-A1 40 33 928 (Henkel).

It is known even from the production of "pure" alkyl oligoglycosides that they are heavily discolored after removal of the excess fatty alcohol and have to be treated with bleaching agents. The same problems affect—albeit not to the same extent—compounds which, in addition to the alkyl and/or alkenyl oligoglycosides, contain the excess fatty alcohol as second component. In this case, too, bleaching with a peroxide is generally necessary for the production of light-colored products marketable for cosmetic purposes.

Another problem which is also known from the production of alkyl oligoglycosides are the long reaction times and the resulting correspondingly long reactor possession times. As already mentioned, it has been found to be necessary to minimize the content of free unreacted glucose in the reaction mixture because it can decompose during the distillation step and can give rise to color-producing components. In addition, significant amounts of unwanted higher oligomers (degree of condensation>2) up to and including polyglucose can be formed.

However, since removal of the fatty alcohol by distillation is expressly not included in the production of the nonionic emulsifiers according to the invention, free fatty alcohol being intended to remain in the mixture, applicants have attempted to limit the conversion and to terminate the reaction after a certain time. Although comparatively light-colored products with a smaller content of higher oligomers are obtained in this way, they still do not meet the high quality requirements which cosmetic starting materials are expected to satisfy.

Accordingly, the problem addressed by the present invention was to provide nonionic emulsifiers containing alkyl and/or alkenyl oligoglycosides and fatty alcohols which would be distinguished by high color quality and a low percentage content of polysugars. At the same time, the reaction times would be significantly shortened.

DESCRIPTION OF THE INVENTION

The present invention relates to nonionic emulsifiers obtained by a) subjecting sugars or water-containing starch degradation products and primary alcohols in a molar ratio of 1:2 to 1:8 and preferably 1:2.5 to 1:4 to acid-catalyzed acetalization in known manner, b) terminating the reaction at a conversion in the range from 60 to 90% of the theoretical, c) neutralizing the reaction product and purifying it with back-mixing of the filtrate through a coarse filter until the filtrate appears clear.

It has surprisingly been found that light-colored mixtures of alkyl and/or alkenyl oligoglycosides and the corresponding fatty alcohols with a small percentage content of higher oligomers and polysugars can be obtained in shortened reaction times if the reaction time and hence the conversion are limited as described and the products are hot-filtered with back-mixing after neutralization. The invention includes the observation that both color-producing constituents and oligomers are adsorbed onto the unreacted glucose—the principal constituent of the filter cake—so that a clear, colorless filtrate with a reduced content of higher oligomers or polysugars is obtained after repeated back-mixing.

The present invention also relates to a process for the production of nonionic emulsifiers in which a) sugars or water-containing starch degradation products and primary alcohols in a molar ratio of 1:2 to 1:8 and preferably 1:2.5 to 1:4 are subjected to acid-catalyzed acetalization in known manner, b) the reaction is terminated at a conversion in the range from 60 to 90% of the theoretical, c) the reaction product is neutralized and purified with back-mixing of the filtrate through a coarse filter until the filtrate appears clear.

Starting Materials

The starting materials used for the acetalization include sugars containing 5 to 6 carbon atoms, preferably glucose. Water-containing starch degradation products, such as for example glucose syrup with a solids content of 70 to 90% by weight and a monoglucose content (DP1 degree) of 90 to 99% by weight, are also suitable.

Suitable primary alcohols are fatty alcohols corresponding to formula (I)

$$R^1\text{—OH} \tag{I}$$

in which $R^1$ is a linear or branched alkyl and/or alkenyl radical containing 12 to 22 carbon atoms. Typical examples are lauryl alcohol, myristyl alcohol, cetyl alcohol, palmitoleyl alcohol, stearyl alcohol, isostearyl alcohol, oleyl olcohol, elaidyl alcohol, petroselinyl alcohol, arachyl alcohol, gadoleyl alcohol, behenyl alcohol, erucyl alcohol and technical mixtures thereof such as are formed, for example, in the high-pressure hydrogenation of technical methyl ester fractions or aldehydes from Roelen's oxo synthesis. Fatty alcohols containing 16 to 18 carbon atoms are preferred from the applicational point of view. Alkyl oligoglucosides containing 16 carbon atoms in the alkyl radical and fatty alcohols containing 18 carbon atoms are particularly advantageous from the point of view of emulsifying power. To obtain a compound having optimal performance properties, it has proved to be suitable to use cetostearyl alcohol as the fatty alcohol component.

Acetalization

The acetalization may be carried out in known manner, for example by initially introducing the sugar and removing the water present therein, adding the calculated excess of fatty alcohol, heating to around 70° to 80° C. and continuously introducing the acidic catalyst, preferably dissolved in another portion of fatty alcohol. The acetalization is normally carried out at temperatures in the range from 100° to 110° C. and under reduced pressure (typically 20 mbar). To displace the reaction towards the desired products, it is also useful continuously to remove the water of condensation from the equilibrium. The end point of the reaction, i.e. the desired conversion, can be calculated via the ratio between the amount of water of condensation removed and the theoretically possible quantity. A conversion of 60 to 90% of the theoretical is sought in accordance with the invention, a value of 70 to 80% and preferably around 75% of the theoretical having proved to be optimal. It is obvious in this regard that a predetermined alkyl and/or alkenyl oligoglycoside content for the surfactant compound can be established both through the fatty alcohol excess and through the conversion. With a large excess of fatty alcohol, a defined content of acetalization product in the compound is achieved at, comparatively, a higher conversion than vice versa. However, the balancing of these two parameters is within the scope of routine optimization work and may be carried out by the expert without any need for inventive activity.

For example, nonionic emulsifiers with a $C_{16/18}$ alkyl and/or alkenyl oligoglycoside content of approximately 22% by weight may be obtained in accordance with the invention where glucose and $C_{16/18}$ fatty alcohol are used in a molar ratio of 1:2.8 and with a conversion of 75% of the theoretical.

Working Up

After termination of the acetalization—by cooling of the reactor and/or breaking of the vacuum—the acidic reaction mixture is neutralized by addition of a base, for example sodium hydroxide and/or magnesium oxide, and adjusted to a pH value of 6 to 7. The unreacted glucose is then filtered off at temperatures in the range from 70° to 95° C. and preferably at temperatures in the range from 80° to 90° C., normally using a pressure filter of conventional design. In the process according to the invention, the filtrate has to be circulated to ensure adequate back-mixing so that a filter cake can build up on which color-producing constituents, higher oligomers and polysugars are adsorbed. In one particular embodiment of the invention, the filtrate may even be circulated between various filter units. Suitable filters are, for example, Seitz filter-medium filters with a pore width of 10 to 1,000 μm.

The end point of the filtration cycle is reached when the filtrate appears clear and no further improvement in color quality can be observed.

Industrial Applications

The nonionic emulsifiers according to the invention may contain 25 to 40% by weight alkyl and/or alkenyl oligoglycosides and 75 to 60% by weight fatty alcohol. The average degree of polymerization of the glucoside component may be 1 to 10, preferably 1 to 3 and more preferably 1.1 to 1.9.

The nonionic emulsifiers are light-colored and highly compatible with the skin and promote the mixing of phases otherwise immiscible with one another. The low content of higher oligomers and polysugars is a particular advantage over known products in this regard.

Accordingly, the present invention also relates to their use for the production of surface-active preparations, for example laundry detergents, dishwashing detergents and cleaning products and, in particular, hair-care and personal hygiene products in which they may be present in quantities of 1 to 50% by weight and preferably in quantities of 3 to 25% by weight, based on the particular preparation. Typical examples in this connection are hair shampoos, bath oils and body lotions and creams.

The following Examples are intended to illustrate the invention without limiting it in any way.

EXAMPLES

Example 1

1. Preparation of catalyst. In a 500 l stirred reactor, 208 kg (812 mol) cetostearyl alcohol (Lanette®O, Henkel KGaA, Düsseldorf/FRG) were heated to 70° C. after which 7.12 kg (36 mol) sulfosuccinic acid in the form of a 70% by weight aqueous solution were added with stirring. The initially homogeneous mixture was stirred at 70° C. until the sulfosuccinic acid had completely dissolved (approx. 10 mins.).

2. Acetalization. In a 10 m³ reactor equipped with a liquid feed inlet, a stirrer and a distillation column, 6184 kg (24.156 mol) cetostearyl alcohol (flaked product) were melted at approx. 70° C. and 1600 kg (8888 mol) anhydrous glucose were added to the resulting melt. After a vacuum of 20 mbar had been applied, the temperature was increased to 105° C. The catalyst solution from (1) was then continuously added over a period of 30 minutes and the water of reaction was distilled off into a receiver. After 5 to 6 h when a conversion of approx. 75% had been reached (as determined through the theoretically possible quantity of water of condensation), the reactor was cooled to 85° C., the vacuum was removed and the reaction was terminated.

3. Working up. The acidic acetalization product was neutralized over a period of 2 h with addition of 0.64 kg magnesium oxide and adjusted to pH 6.5. The mixture was then filtered through a coarse filter (pore width 10 μm) at a temperature of approx. 90° C. and under a pressure of 2 bar. The filtrate was continuously pumped back into the reaction mixture to ensure back-mixing. 368 kg filter cake and 6824 kg filtrate were obtained. The results are set out in Table 1.

Comparison Example C1

Example 1 was repeated. The acetalization product was neutralized and filtered through a coarse filter, but with no back-mixing. The results are set out in Table 1.

Comparison Example C2

Example 1 was repeated except that the reaction was terminated after 8 h at a conversion of approx. 99%. The acetalization product was neutralized and filtered through a coarse filter with back-mixing. The results are set out in Table 1.

Comparison Example C3

Example 1 was repeated except that the reaction was terminated after 8 h at a conversion of approx. 99%. The acetalization product was neutralized and filtered through a coarse filter, but with no back-mixing. The results are set out in Table 1.

TABLE 1

| | | | Test Results | | | | |
|---|---|---|---|---|---|---|---|
| | C | t | Composition (% by weight) | | | | Color |
| Ex. | % | h | FA | DP1 | DP2 | DPX | Rest | Klett |
| 1 | 75 | 5 | 67.7 | 14.9 | 3.8 | 1.4 | 12.2 | 15 |
| C1 | 75 | 5 | 64.8 | 14.1 | 3.9 | 2.1 | 15.1 | 75 |
| C2 | 99 | 8 | 66.3 | 12.8 | 3.6 | 5.3 | 12.0 | 190 |
| C3 | 99 | 8 | 66.3 | 10.9 | 3.8 | 6.8 | 13.1 | 210 |

Legend:
C = Conversion
t = Reaction time
FA = Fatty alcohol
DP1 = Monoglucoside
DP2 = Diglucoside
DPX = Oligoglucoside
Color = Color value, as measured in a Klett photometer, samples 30% by weight in toluene, 4 cm cell.

We claim:

1. A process for making nonionic emulsifiers comprising:
   (a) performing an acid-catalyzed acetalization reaction on a mixture of (i) sugars or water-containing starch degradation products and (ii) primary alcohols in a molar ratio of (i):(ii) of from 1:2 to 1:8;
   (b) terminating said reaction at a conversion ranging from 60 to 90% of the theoretical to form a reaction product;
   (c) neutralizing said reaction product to form a neutralized reaction product; and
   (d) purifying said neutralized reaction product by back-mixing said product through at least one coarse filter until said product becomes clear.

2. The process of claim 1 wherein said sugars comprise glucose.

3. The process of claim 1 wherein said primary alcohols correspond to formula (I):

$$R^1\text{—OH} \qquad (I)$$

wherein $R^1$ is selected from the group consisting of a linear alkyl radical containing from 12 to 22 carbon atoms, a branched alkyl radical containing from 12 to 22 carbon atoms, a linear alkenyl radical containing from 12 to 22 carbon atoms, a branched alkenyl radical containing from 12 to 22 carbon atoms, and mixtures thereof.

4. The process of claim 1 wherein said step (d) is performed at a temperature ranging from 70° C. to 95° C.

5. The process of claim 1 wherein said molar ratio of (i):(ii) is from 1:2.5 to 1:4.

6. The process of claim 1 wherein said water-containing starch degradation products comprise glucose syrup having a solids content of from 70% to 90% by weight, and a monoglucose content of from 90% to 99% by weight, all weights being based on the weight of said glucose syrup.

7. The process of claim 1 wherein said primary alcohols comprise fatty alcohols having from 16 to 18 carbon atoms.

8. The process of claim 1 wherein said step (a) is performed at a temperature ranging from 100° C. to 110° C. and a pressure of 20 mbar.

9. The process of claim 1 wherein said neutralized reaction product of said step (c) has a pH of from 6 to 7.

10. The process of claim 1 wherein multiple coarse filters are employed in said step (d).

* * * * *